United States Patent
Ramanand et al.

(10) Patent No.: US 10,485,887 B2
(45) Date of Patent: Nov. 26, 2019

(54) TARGETED SURFACE DISINFECTION SYSTEM WITH PULSED UV LIGHT

(71) Applicants: Prakash Valentino Ramanand, Burlington (CA); Manjinder Singh Dhillon, Milton (CA); Adam Ray Steinhoff, Toronto (CA); Vinod K. Menon, Merrimack, NH (US)

(72) Inventors: Prakash Valentino Ramanand, Burlington (CA); Manjinder Singh Dhillon, Milton (CA); Adam Ray Steinhoff, Toronto (CA); Vinod K. Menon, Merrimack, NH (US)

(73) Assignee: Angelica Holdings LLC, Dover, DE (US)

( * ) Notice: Subject to any disclaimer, the term of this patent is extended or adjusted under 35 U.S.C. 154(b) by 0 days.

(21) Appl. No.: 15/095,212

(22) Filed: Apr. 11, 2016

(65) Prior Publication Data
US 2016/0296649 A1 Oct. 13, 2016

Related U.S. Application Data

(60) Provisional application No. 62/146,299, filed on Apr. 12, 2015.

(51) Int. Cl.
*A61L 2/10* (2006.01)
*A61L 2/28* (2006.01)

(52) U.S. Cl.
CPC .................. *A61L 2/10* (2013.01); *A61L 2/28* (2013.01); *A61L 2202/11* (2013.01);
(Continued)

(58) Field of Classification Search
CPC .................................. A61L 2/10; A61L 2/28
See application file for complete search history.

(56) References Cited

U.S. PATENT DOCUMENTS

| 5,330,722 A | 7/1994 | Pick |
| 5,426,308 A | 6/1995 | Sudduth |
(Continued)

FOREIGN PATENT DOCUMENTS

| RU | 2031659 C1 | 3/1995 |
| WO | 2002058744 A1 | 8/2002 |
(Continued)

OTHER PUBLICATIONS

Stibich, Mark "Evaluation of a Pulsed-Xenon Ultraviolet Room Disinfection Device for Impact on Hospital Operations and Microbial Reduction". Infection Control and Hospital Epidemiology, Mar. 2011, vol. 32, No. 3.

*Primary Examiner* — Regina M Yoo
(74) *Attorney, Agent, or Firm* — Seth Natter; Natter & Natter

(57) ABSTRACT

A pulsed UV disinfection system includes a xenon UV lamp mounted in an articulated head assembly and a chassis housing a high voltage power supply for driving the lamp and a pulse configuration control unit for configuring the output of the power supply. The head assembly and the chassis are positioned on a mobile carriage. The pulse configuration control unit is programmed for driving the UV lamp at a rate of between 20 and 50 pulses per second, with each pulse emitting between 30 and 150 joules of UV radiant energy. The system also features remote video imaging of a target area, remote control of the carriage and head assembly as well as a remote emergency shutdown.

20 Claims, 13 Drawing Sheets

(52) U.S. Cl.
CPC ....... *A61L 2202/14* (2013.01); *A61L 2202/16* (2013.01); *A61L 2202/25* (2013.01)

(56) References Cited

U.S. PATENT DOCUMENTS

| | | | |
|---|---|---|---|
| 6,692,694 B1* | 2/2004 | Curry | A61L 2/088 422/1 |
| 7,380,627 B2 | 6/2008 | Huang | |
| 7,834,335 B2 | 11/2010 | Harmon | |
| 7,930,066 B2* | 4/2011 | Eliuk | A61J 1/20 221/191 |
| 8,277,724 B2 | 10/2012 | Jung | |
| 8,872,669 B2 | 10/2014 | Stibich | |
| 9,093,258 B2 | 7/2015 | Stibich | |
| 9,165,756 B2 | 10/2015 | Stibich | |
| 9,603,956 B2 | 3/2017 | Newham | |
| 2004/0028553 A1 | 2/2004 | Panico | |
| 2005/0143793 A1* | 6/2005 | Korman | A61N 5/0616 607/94 |
| 2006/0216193 A1 | 9/2006 | Johnson | |
| 2009/0272029 A1* | 11/2009 | Aiking | A01N 3/00 47/1.43 |
| 2010/0000948 A1* | 1/2010 | Park | A61L 2/10 210/748.11 |
| 2011/0305597 A1* | 12/2011 | Farren | A61L 2/10 422/24 |
| 2013/0330235 A1 | 12/2013 | Stibich | |
| 2014/0241941 A1* | 8/2014 | Kreitenberg | A61L 2/10 422/24 |
| 2015/0064065 A1 | 3/2015 | Kreitenberg | |
| 2015/0086520 A1 | 3/2015 | Steriliz | |

FOREIGN PATENT DOCUMENTS

| | | |
|---|---|---|
| WO | 2003061382 A1 | 7/2003 |
| WO | 2015116876 A1 | 8/2015 |
| WO | 2016044759 A1 | 3/2016 |

* cited by examiner

TARGETED SURFACE DISINFECTION SYSTEM WITH PULSED UV LIGHT

RELATED APPLICATION

This application claims the benefit of U.S. Provisional Application No. 62/146,299, Filed Apr. 12, 2015, the entirety of which is incorporated herein by reference.

BACKGROUND OF THE INVENTION

1. Field of the Invention

The present invention relates generally to systems and methods for disinfection and decontamination of surfaces and, in particular, to systems and methods which employ pulses of Ultra Violet (UV) light for surface disinfection and decontamination.

2. Antecedents of the Invention

UV radiation has been employed for disinfection and decontamination of surfaces, air and liquids. It is considered to be one of the best non-contact decontamination processes. The UV-C region of the UV spectrum has been found to be the most lethal to microorganisms; the strongest germicidal effects have been reported to be in the wave-length from 200 nm to 280 nm. This part of the spectrum has been found lethal to several ranges of microorganisms.

Traditionally, UV radiation for disinfection employed medium pressure mercury vapor lamps to generate UV radiation. In recent decades, pulsed xenon lamps have been found to be much more effective than other UV light emitting technology.

There are several reasons which play a critical role in the efficacy of pulsed xenon UV radiation used for disinfection. One is the broadband spectrum of UV discharge in xenon lamps.

Another reason is that pulsed xenon UV systems have the capability of discharging several megawatts of UV energy in micro-seconds or milliseconds, causing irreversible changes in the cellular level in the microorganisms exposed.

Pulsed xenon UV light technology was first developed in Japan. In 1984 Hiramoto patented pulsed UV light technology for sterilization applications. Since then it has been employed for various applications involving disinfection and decontamination The spectral output of an UV xenon lamp is very similar to that of sunlight. It goes from 180 nm to 1100 nm, with some major spikes in visible region of the spectrum. The xenon UV discharge lamp can be designed in different geometries to best fit the application. That makes the pulsed UV system very flexible. The system can be tailored to best fit the application in terms of energy requirement.

The energy dissipated can be controlled in terms of number of pulses, energy per pulse and pulse width. Since the xenon UV flash tube discharges in pulses, the existing systems are not a good fit for applications involving fast moving targets.

Characteristics of Pulsed UV Light Relevant to Disinfection

Pulsed light energy is measured in fluence and is related to fluence rate. Fluence rate is the total radiant energy falling on small transparent sphere containing the target from all possible directions, divided by the cross section of the target. It is generally expressed in W/m2.

Fluence can be defined as the product of fluence rate, exposure time in seconds and total amount of energy incident on the target during the exposure time. It is expressed in $J/m^2$ or $J/cm^2$.

$$F = e * t * f$$

Where F is the fluence ($J/cm^2$), "e" is the energy per pulse J/cm2/pulse, "t" is the time in seconds and "f" is the frequency.

A well-known general rule in photochemistry, the Bunsen-Roscoe reciprocity law, states that the extent of photochemical effects on living beings is determined by cumulative irradiance. Accordingly, for disinfection applications, the current methods and apparatuses using pulsed UV light technology tend to employ high UV energy per pulse, and relatively low frequencies of 1-2 pulses per second.

Typical prior art systems employing pulsed xenon UV lamps for disinfection are disclosed in U.S. Pat. Nos. 9,093,258, 8,872,669 and 9,165,756 as well as U.S. Patent Application Publication No. 2013-0330235. These systems suffered from various shortcomings, however.

They employed lower pulse frequency (typically below 2 Hz), therefore took longer time to inactivate germs. They employed high discharge energy per each pulse (typically more than 500 joules), therefore the generated noise level was high (manifested as loud popping sounds) causing disturbance around the treated area. The high energy of discharge also generated an unsafe amount of ozone, which had to be removed by specialized fans and filters, contributing to additional cost, complexity and noise. They employed a 360 degree, all around flashing UV light geometry, making them suitable for entire room disinfection, but causing energy to be wasted if only certain limited surfaces were in need of treatment. To compensate for the wasted energy, they required more operating time in each room, hence relatively high overall energy consumption. Due to their high level of ozone generation, they required additional filtration and power consuming auxiliary components such as blower motors, etc., which resulted in higher energy consumption per unit time. They employed optical filters (to filter out the visible light produced by the lamps), which did not fully eliminate visible pulsating light while decreasing the UV capability of the apparatus.

Thus, there was an unmet need for systems and methods of pulsed xenon UV disinfection that do not suffer from the shortcomings of the antecedents referenced above. There was a further need for such systems to work more rapidly, to be able to focus more effectively only on certain targeted contaminated surfaces, and to be more energy efficient.

SUMMARY OF THE INVENTION

The present invention responds to this unmet need by providing systems and methods which enable targeted surface decontamination and room disinfection capabilities. A mobile pulsed xenon UV disinfection unit includes an articulated head assembly carrying a xenon UV lamp or lamps and a parabolic reflector. The pulsed xenon UV disinfection unit further includes a high voltage power supply and a pulse configuration control unit, which are mounted in a chassis.

The chassis is seated on a robotic mobile carriage or platform and is housed within a cabinet. The pulse configuration control unit is programmed to drive the xenon UV lamp to emit 30-150 joules of energy per pulse, at a frequency of 20-50 Hz, with a preferred pulse rate of 25-35 Hz. Various software and hardware components are included to achieve additional functionality such as remote video imaging of a target area, remote control of the mobile carriage or platform and the articulated movement of the head assembly, a safety emergency shutoff, remote management, reporting, data storage, billing, etc.

From the foregoing compendium, it will be appreciated that a feature of the present invention is to provide a targeted surface disinfection system with pulsed UV light of the general character described which is not subject to the disadvantages of the aforementioned antecedents of the invention.

An aspect of the present is to provide a targeted surface disinfection system with pulsed UV light of the general character described which uses a higher frequency pulsing rate for more effective bombardment of microorganisms.

A consideration of the present is to provide a targeted surface disinfection system with pulsed UV light of the general character described which uses lower discharge energy per pulse, hence generates lower noise and low ozone, to the point where additional ozone filters may not be required.

A further feature of the present invention is to provide a targeted surface disinfection system with pulsed UV light of the general character described which allows the targeted disinfection of just the desired surfaces and areas of a room, with capability for precise control of the amount of UV light that hits each targeted area, and hence it does not waste energy irradiating non-target areas.

Another aspect of the present invention is to provide a targeted surface disinfection system with pulsed UV light of the general character described which requires less time per average room, therefore it has a lower energy consumption which reduces its cost of operation.

A further consideration of the present is to provide a targeted surface disinfection system with pulsed UV light of the general character described wherein a higher percentage of power used is converted into useful UV energy emitted on the targeted surfaces.

A still further aspect of the present invention is to provide a targeted surface disinfection system with pulsed UV light of the general character described which does not require additional optical filters or ozone filters.

BRIEF DESCRIPTION OF THE DRAWINGS

In the accompanying drawings, in which are shown an exemplary embodiment of the present invention.

DETAILED DESCRIPTION OF THE PREFERRED EMBODIMENT

Figure 1:
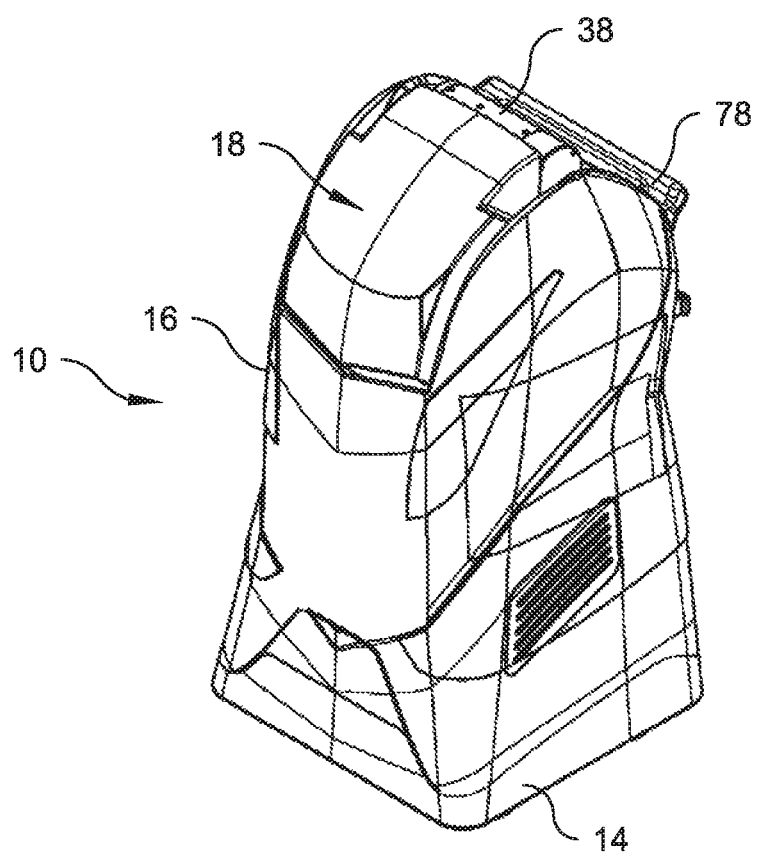
FIG. 1 is an isometric view of a surface disinfection system in accordance with the invention illustrating a cabinet housing a chassis and with an articulated head assembly in a retracted position.

The present invention will now be described in detail with reference to the drawings, which are provided as illustrative examples of the invention so as to enable those skilled in the art to practice the invention. Notably, the figures and examples below are not meant to limit the scope of the present invention to a single embodiment, but other embodiments are possible by way of interchange of some or all of the described or illustrated elements.

Moreover, where certain elements of the present invention can be partially or fully implemented using known components, only those portions of such known components that are necessary for an understanding of the present invention will be described, and detailed descriptions of other portions of such known components will be omitted so as not to obscure the invention. In the present specification, an embodiment showing a singular component should not be considered limiting; rather, the invention is intended to encompass other embodiments including a plurality of the same component, and vice-versa, unless explicitly stated otherwise herein.

Moreover, applicant do not intend for any term in the specification or claims to be ascribed an uncommon or special meaning unless explicitly set forth as such. Further, the present invention encompasses present and future known equivalents to the known components referred to herein by way of illustration.

With reference now to the drawings, wherein like numerals refer to like components throughout, the reference numeral 10 denotes generally a targeted surface disinfection unit with pulsed UV light constructed in accordance with and embodying the invention.

A chassis 12, mounted on a remote controlled robotic mobile carriage or platform 14 is enclosed in a cabinet 16. The cabinet 16 may fabricated of fire-retardant plastic, but any other suitable material can be employed. The mobile carriage or platform 14 is fitted with electric motors connected to floor mobility devices, e.g. wheels, tracks, mecanum wheels, casters, traction wheels, omnidirectional wheels, etc., which allow the entire unit to move (sideways, forward, rotate, backward, etc.,) and to be relocated with precision to any desired target position in a room, allowing navigation around furniture and in tight spaces/corners. Optionally, the wheels can be omnidirectional, for example allowing the unit to move to the sides while facing forward.

A pulsed xenon UV lamp head assembly 18 is supported from the chassis 12 by a pair of parallel vertical columns 20 having a pair of parallel horizontal upper and lower stringers 22, 23. The head assembly 18 is secured to a vertical journal 24 which is seated in registered bearing surfaces 25 of the stringers 22. A motor 26, secured to the lower stringer 23, engages a belt drive 28 to selectively rotate the journal 24, hence the head assembly 18 in a panning motion about a vertical axis.

Figure 3:
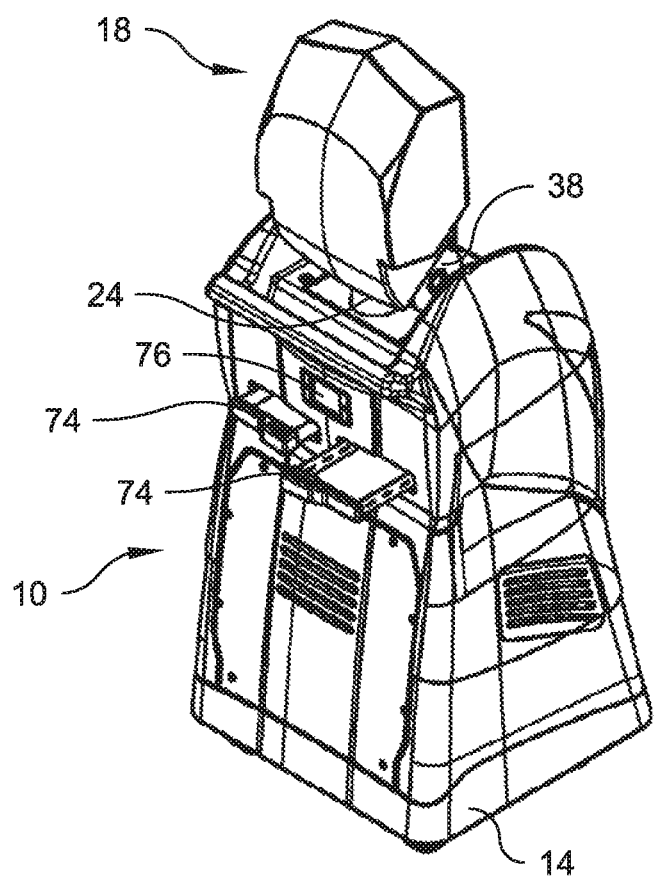
FIG. 3 is a rear isometric view with the head assembly in an operative position.
Figure 4:
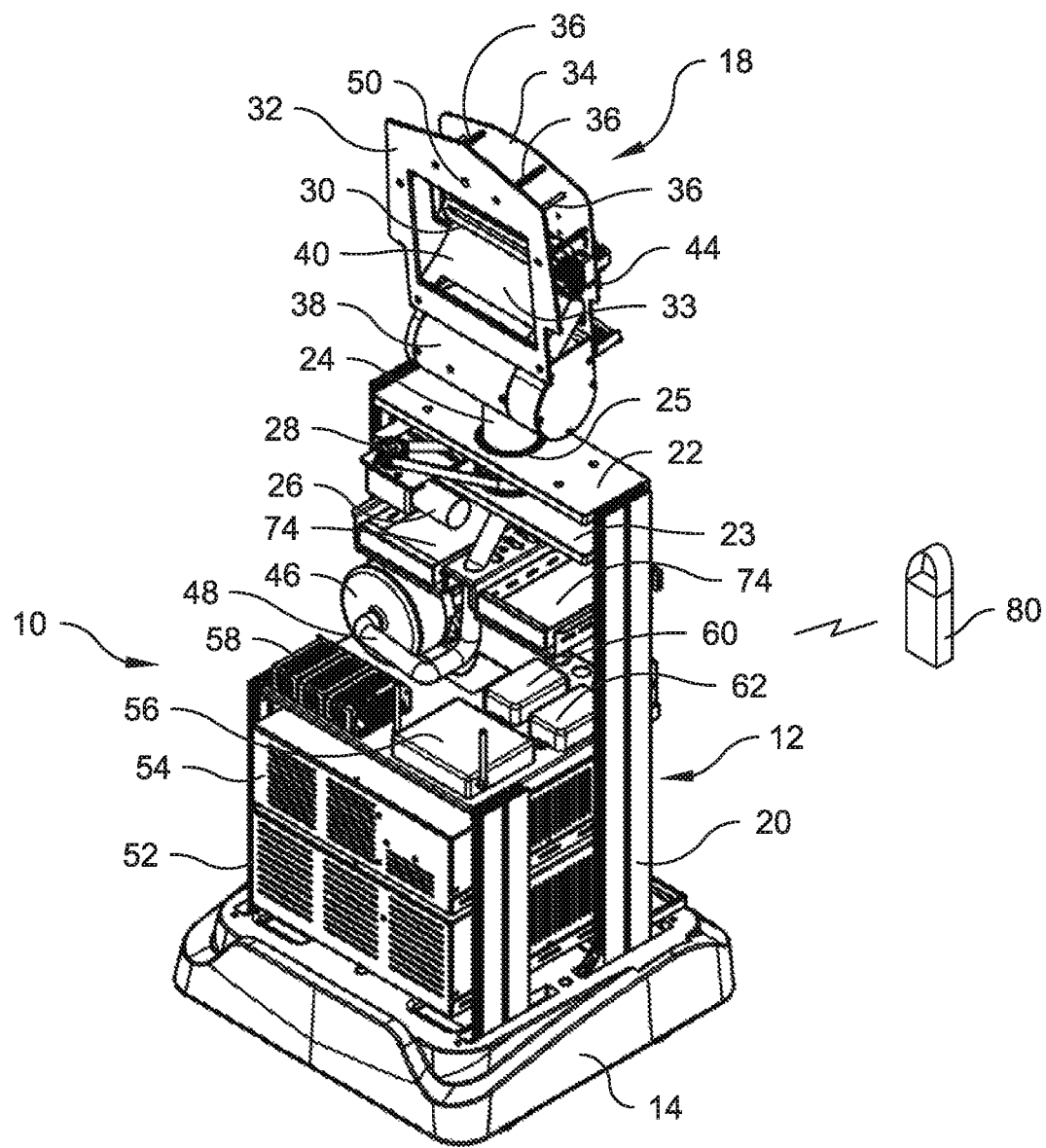
FIG. 4 is an isometric view similar to FIG. 2, but with the cabinet removed.
Figure 5:
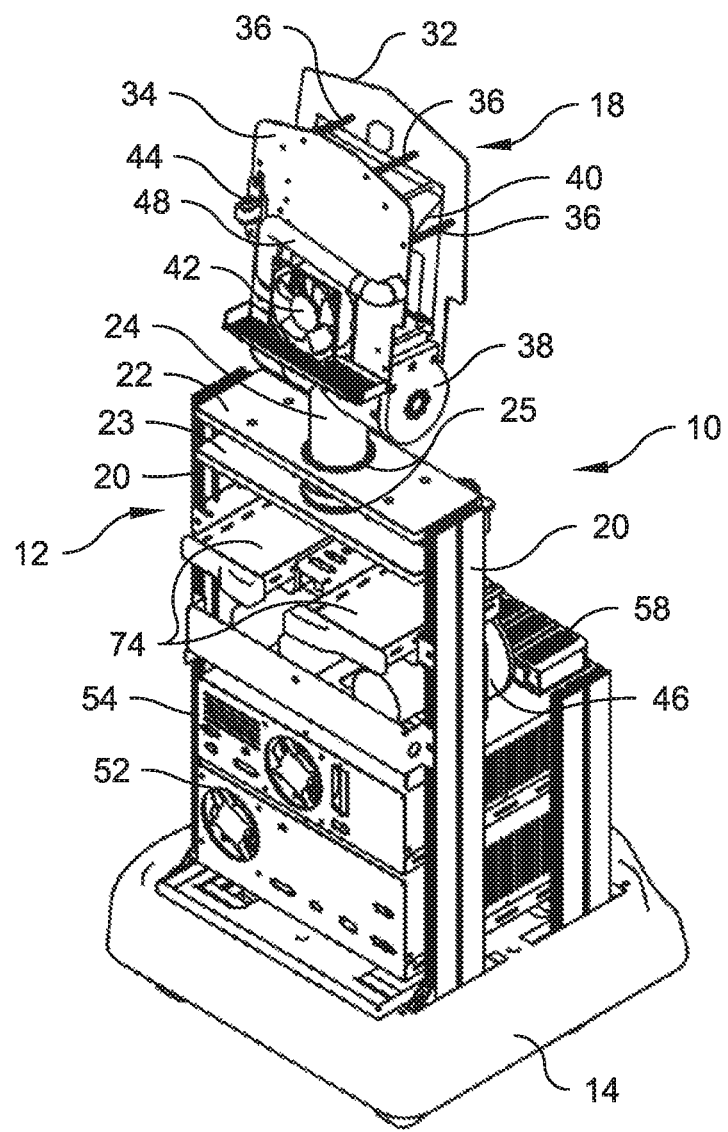
FIG. 5 is a rear isometric view with the cabinet removed.
Figure 6:
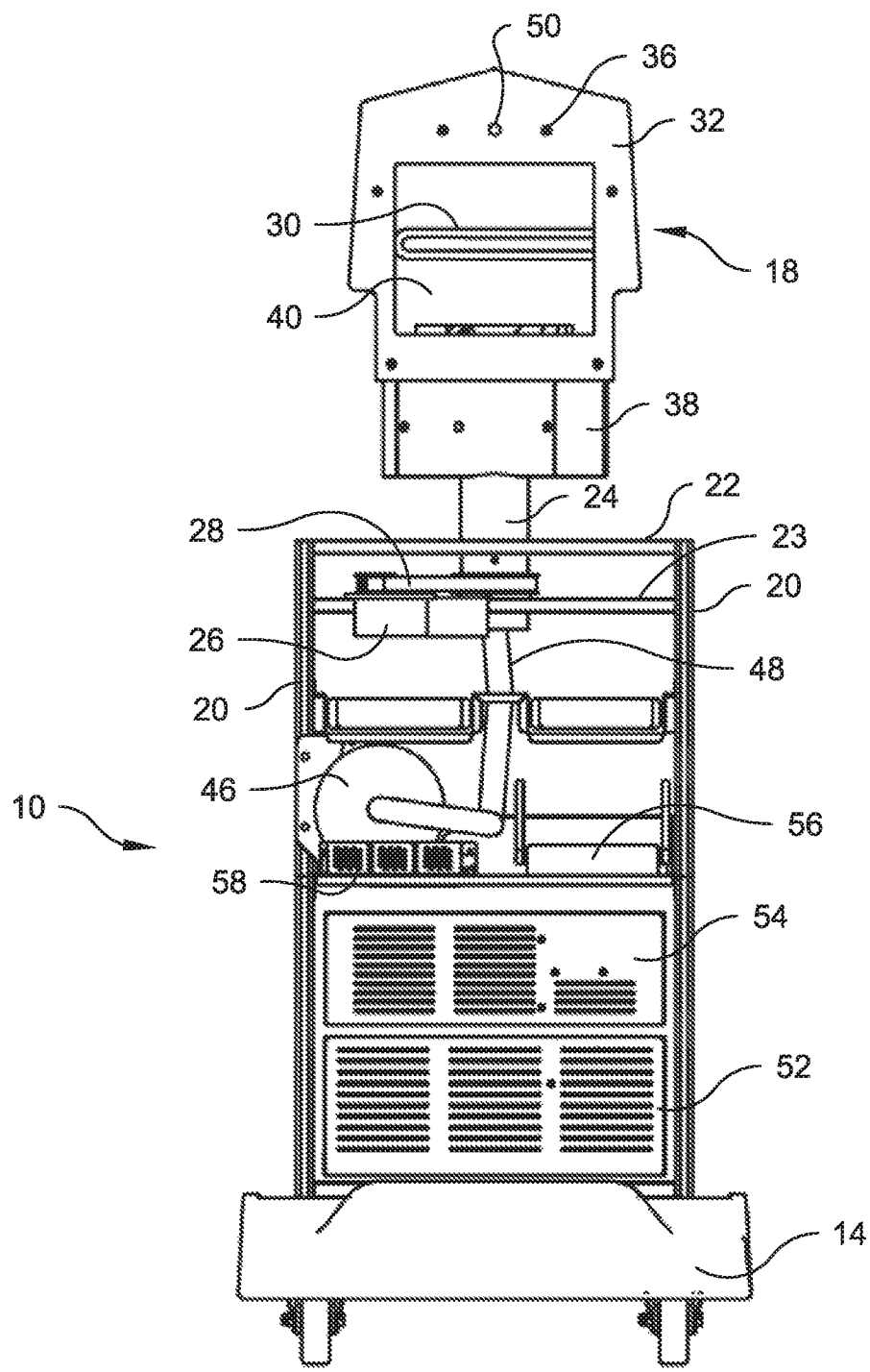
FIG. 6 is a rear elevational view with the cabinet removed.
Figure 7:
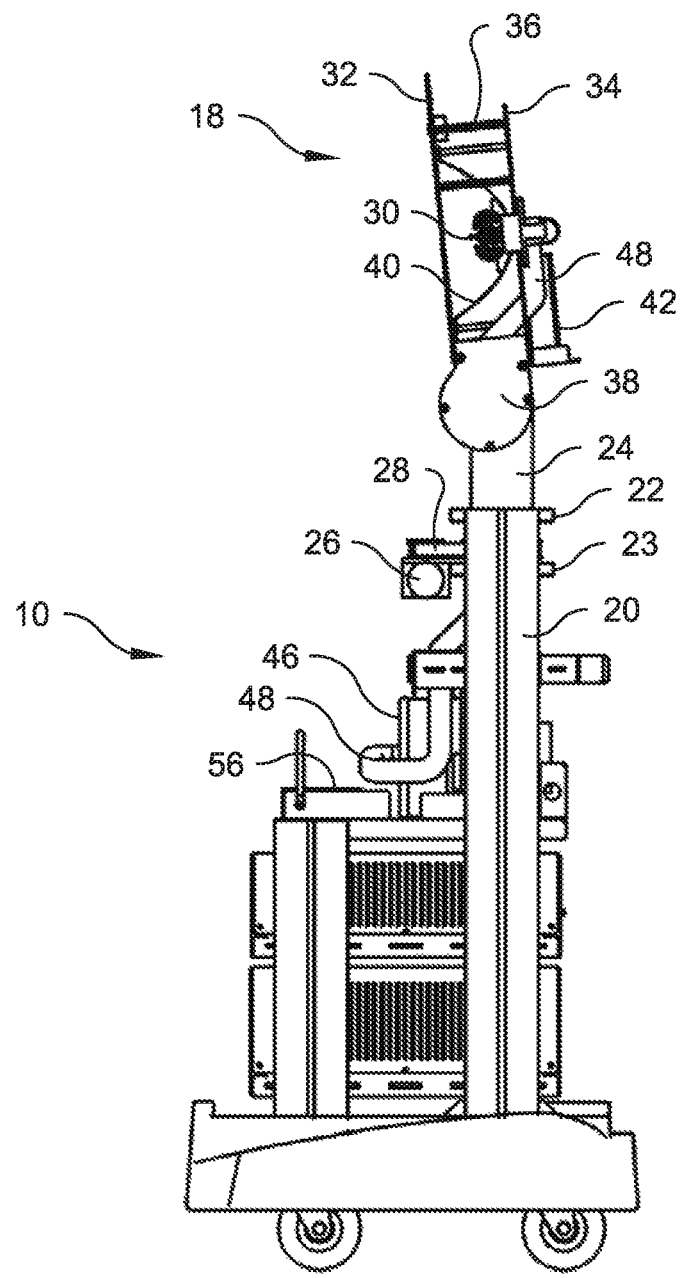
FIG. 7 is a side elevational view with the cabinet removed.

With reference to FIGS. 4 and 6, it will be seen that the head assembly 18 carries a xenon UV lamp 30 mounted between a front panel 32, having an opening with a fused quartz window 33, preferably without optical filters, and a rear panel 34. The front and rear panels are fixed in parallel relationship by a plurality of spacer rods 36 and a motorized tilt mechanism 38 joins the top of the journal 24 to the head assembly 18. The tilt mechanism 38 rotates about a horizontal axis the selectively pivot the head assembly 18 from a retracted position, seated in a recessed portion of the cabinet as illustrated in FIG. 1, to the operative position, shown in FIGS. 2-7, and vice versa and may position the head at any desired angle there between. The tilt mechanism 38, in combination with the belt driven journal 24, allow precise pan, swivel, tilt and rotate movement of the head assembly.

It should also be noted that the head assembly 18 includes a parabolic reflector 40, which reflects the UV light towards the target area. The reflector 40 is mounted directly behind the xenon UV lamp 30, and is fabricated of metal or any suitable material to reflect preferably 95% or more of the light in the UV region of interest to this invention. Positioning the reflector behind the xenon UV lamp 30 helps direct most of the emitted UV light in the direction of the target, instead of dissipating it at 360 degrees around the entire room and thereby conserves energy. The beam generated by the lamp/reflector combination may preferably be wide to maximize coverage of a target area rather than concentrated however other lamp/reflector configurations are possible, with more concentrated beams of UV light.

To dissipate the heat generated by the xenon lamp 30, a fan 42 is positioned at an opening through the rear panel 34 of the head assembly 18 and a heat sink 44 may also employed. Cooling is augmented by creating a negative air pressure within the cabinet 12 to draw in the warm air from the area around the xenon lamp 30 as well as any heat generated by the control electronics and power circuitry carried by the chassis 12. In this regard, a vacuum pump 46 having a suction hose 48, which extends to the rear panel 34, assures that air flow from the head assembly will exhaust through louvered vent openings in the cabinet 16. One or more auxiliary blowers may also be employed expel warm air out of the vent openings, with optional filtration of the exhaust.

A video camera 50, mounted in the front panel 32, is employed to remotely monitor the system in operation and for remotely moving the unit for disinfection of different target areas within the same room. The movement of the mobile platform 14 and the entire operation of the system is remotely controlled by an operator (located at a safe distance, outside the room being disinfected with UV) via a handheld smart device (such as tablet, etc.) wirelessly connected to a wireless hub and to a control unit fitted within the chassis 12. An operator standing outside also has the ability, on his or her tablet, to watch the system in operation through the live-streaming video camera 50 and can also cause the unit to move within the room using a virtual joy stick on the tablet's screen.

The cabinet 16 encloses an electrical power supply and control system for either the mobile carriage or platform 14 and for the xenon UV lamp 30. An external power cord (not shown) is plugged into a suitable electrical outlet in the room for powering the unit. The power cord may be stored on a retractable reel disposed inside the cabinet.

Pursuant to the invention, a high voltage power supply 52, for energizing the xenon lamp 30, is mounted in the chassis 12. A pulse configuration control unit comprising programmable pulse configuration pc boards is positioned in a control card box 54 which is mounted to the chassis 12. Also carried by the chassis 12 is a wireless router or hub 56 for data transfer and communication links with a remote operator and server, a regulated dc power supply 58, a central control unit 60 having an RF transmitter for communication with a door card and programmable motor controller cards 62 for controlling the motor 26 and the motor of the tilt mechanism 38, effecting articulation of the head assembly 18 as well as the motor or motors of the mobile carriage or platform 14. The control card box 54, central control unit 60 and motor controller card 62 will hereinafter collectively be referred to as "control system".

Figure 8:
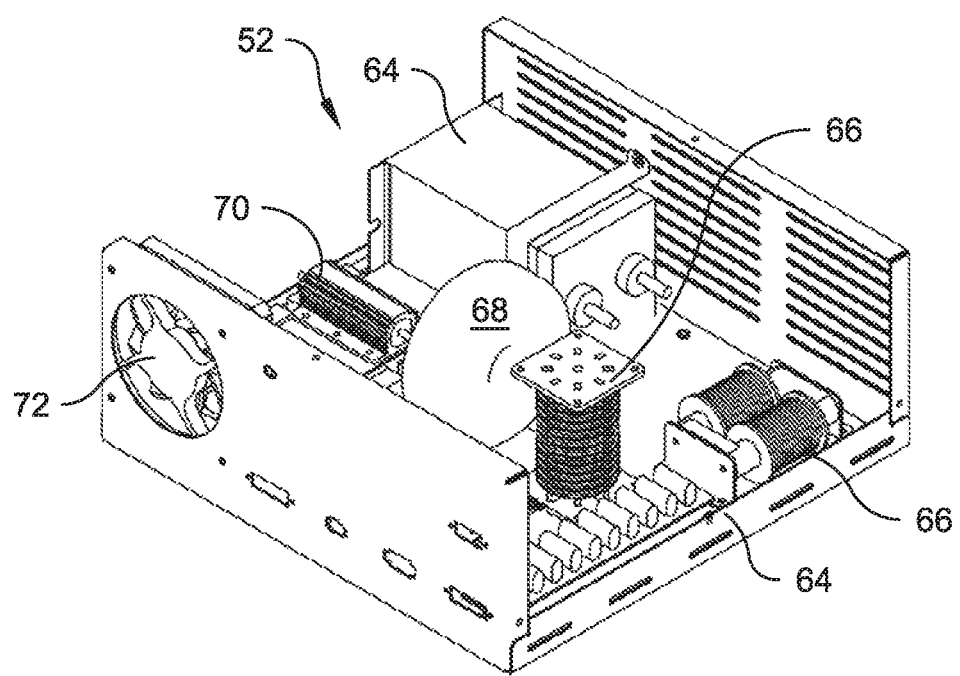
FIG. 8 is an isometric view of a high voltage power supply, with portions of its cabinet removed to better illustrate exemplary components thereof.
Figure 9A:
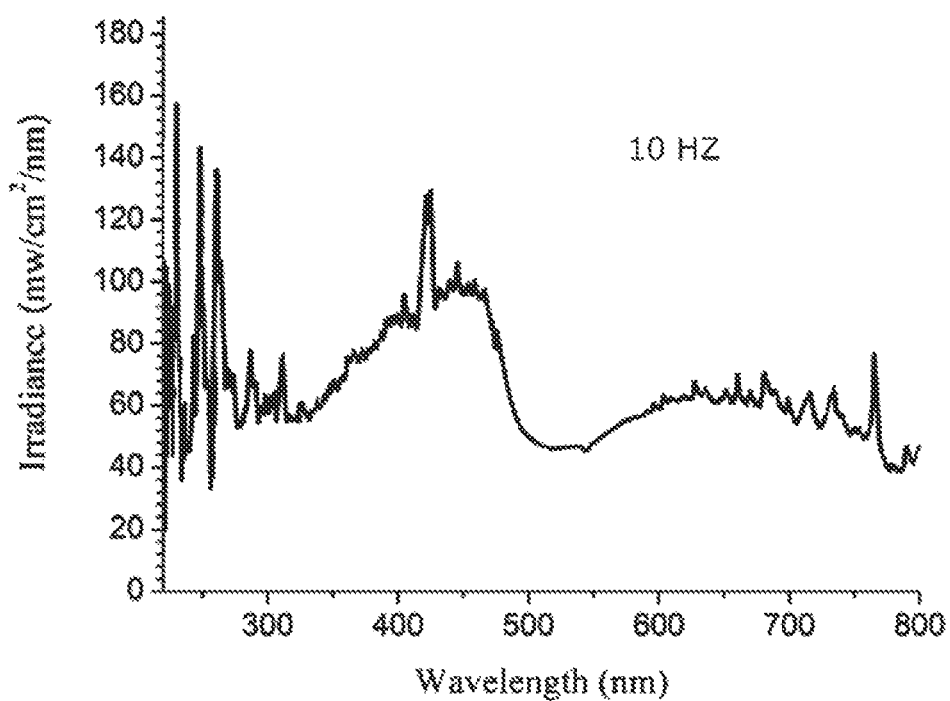
FIG. 9a is a graph of test results indicating xenon lamp energy output at a pulse rate of 10 Hz.
Figure 9B:
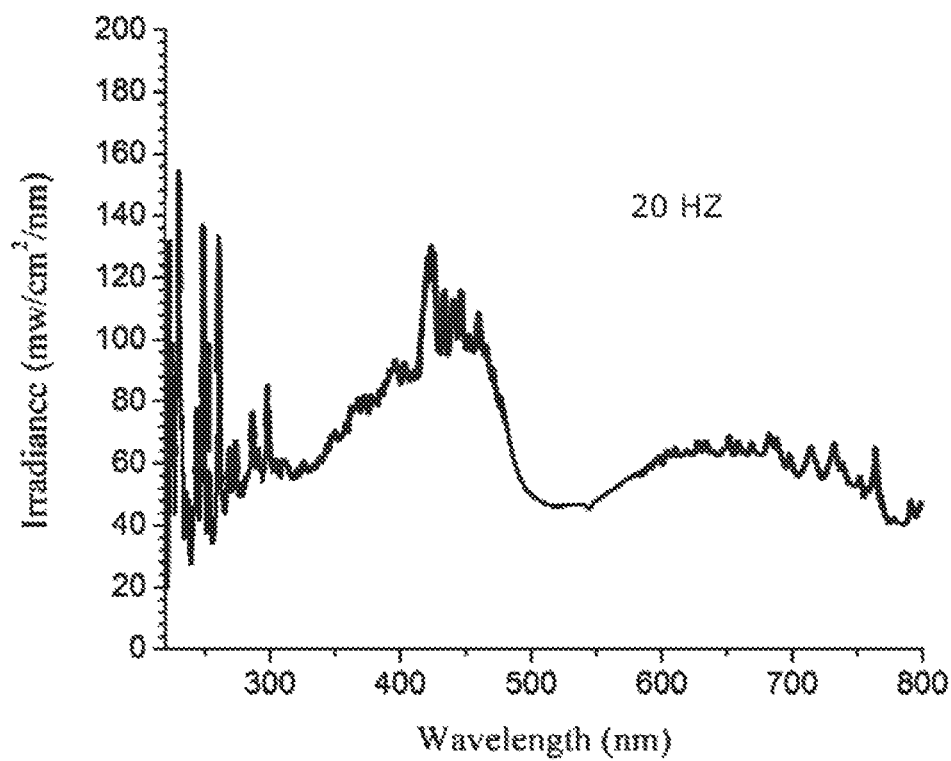
FIG. 9b is a graph of test results indicating xenon lamp energy output at a pulse rate of 20 Hz.
Figure 9C:
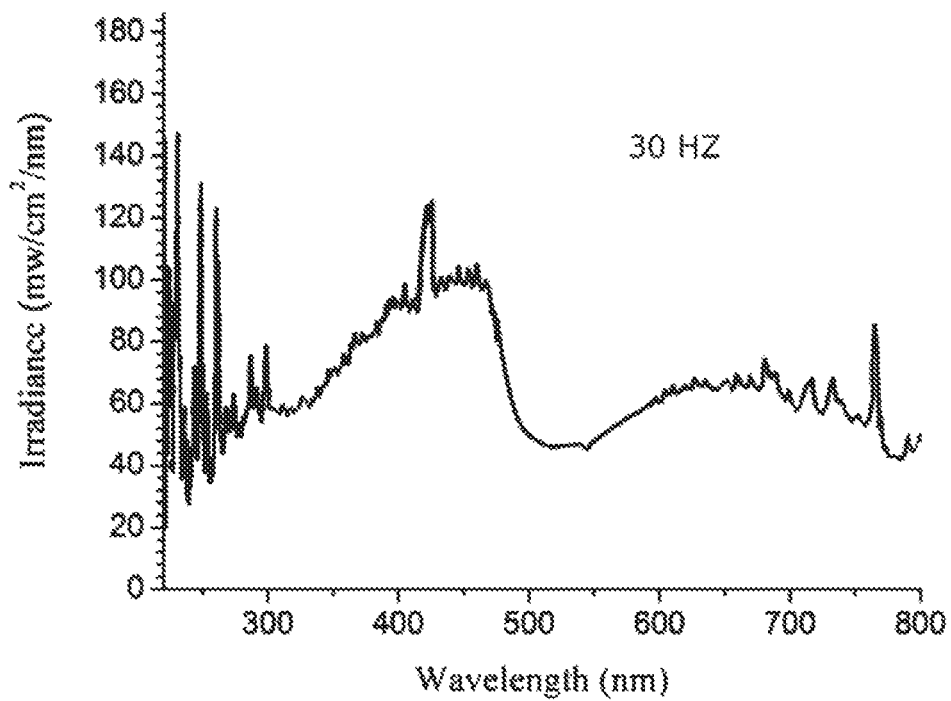
FIG. 9c is a graph of test results indicating xenon lamp energy output at a pulse rate of 30 Hz.
Figure 9D:
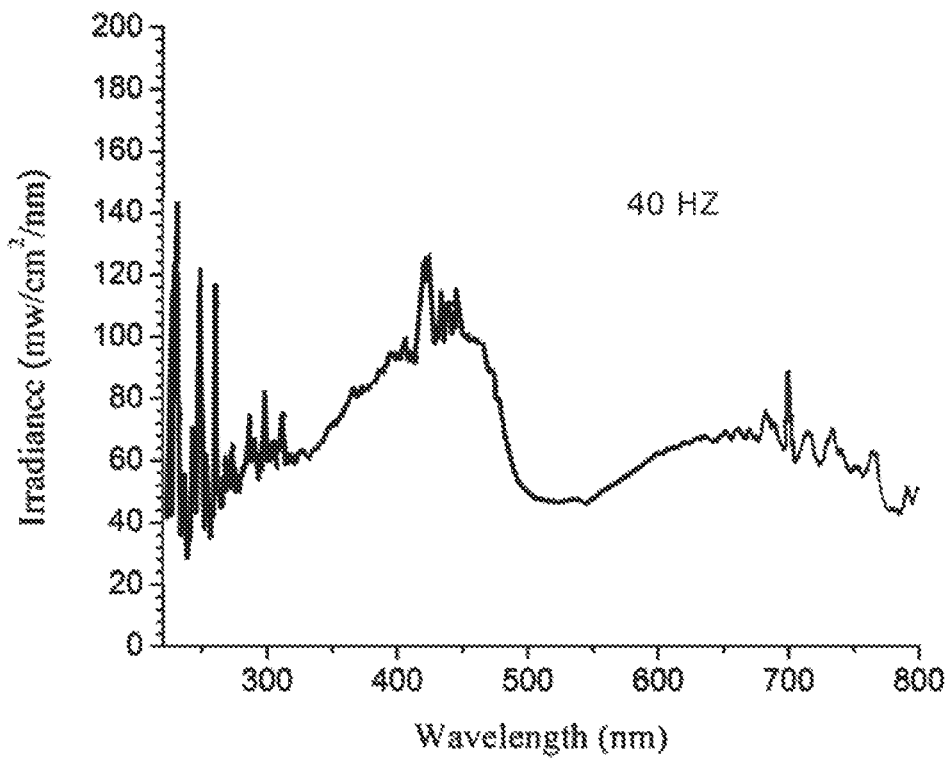
FIG. 9d is a graph of test results indicating xenon lamp energy output at a pulse rate of 40 Hz.
Figure 9E:
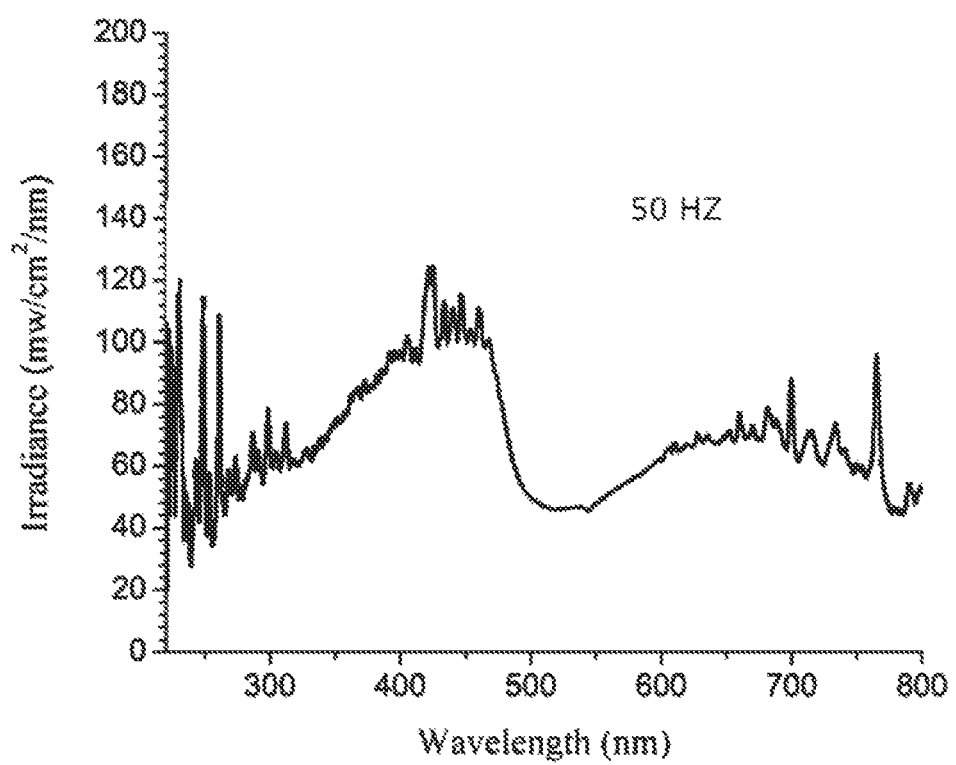
FIG. 9e is a graph of test results indicating xenon lamp energy output at a pulse rate of 50 Hz.

Referring now to FIG. 8, wherein components of the high voltage power supply 52 are depicted within a housing, energy is stored in a high power capacitor 64 for a relatively long period, e.g. a fraction of a second, from which it is released with a shorter time, e.g. nanoseconds to milliseconds, resulting in intense pulses of light generated by the xenon lamp 30 focused on the target treatment area. Also included in the housing is a transformer 68, is a capacitor bank 65, inductors 66, a resistor 70 and a cooling fan 72.

An LCD screen 76, fitted with touch screen capability or other input controls, is mounted at the rear of the cabinet 16, enables an administrator to review and interface with the operating parameters and to manually control/adjust/program various operating parameters, such as: the frequency of the UV Pulse, the duration of the flashing cycle and to toggle between various modes of flash, etc. The LCD screen graphical interface preferably has capability for being password protected or implements other credential-based login systems that only allow authorized personnel to operate it for programming, repair or diagnostics.

One or more access panels on the cabinet allow access to all components (motors, servos, electronics, robotics, structural members, blowers, etc.) disposed inside the cabinet, for assembly and maintenance purposes. Various storage slots and holders can be optionally fitted on or in the cabinet to hold or store various attachments, such as the remote control tablet, various auxiliary safety devices, e.g., emergency shut-off switches, both wireless and manual, may also be located at convenient positions on or in the cabinet or may be stored in pull out trays 74.

The cabinet may also include a handle 78, illustrated in FIG. 1, enabling an operator to manually manoeuver the unit from room to room.

The operator located outside the room being disinfected has the ability, on his or her tablet, to remotely pan, swivel and tilt the head assembly 18 in order to precisely direct the UV beam to the area targeted for disinfection. By being able to be positioned close to the target area, no matter how small such target area is, and to treat that area with a concentrated beam of UV light, the present invention is uniquely suited for spot disinfection of high-touch surfaces in rooms, hospitals, nursing homes and other places.

When not in operation for UV disinfection, the head assembly 18 retracts or folds inside a recess provided in the upper section of the cabinet 12. With the head assembly tucked in its retracted configuration, the entire unit is more maneuverable and easier to move around, and the fragile components, especially the xenon UV flash lamp in the head assembly, are more protected during moving, transport and storage.

If ozone by-production by the UV flash lamp is a concern, which might only be expected at high lamp power levels, the same cooling system can be optionally adapted to also remove the ozone by-product, by fitting ozone filters within the path of the cooling air stream exhausted by the vacuum pump. Normal dust air filters can also be optionally fitted.

The air stream drawn from the head assembly 18 may also be employed to cool the control electronics mounted to the chassis 12.

The xenon UV flash lamp 30 can comprise a commercially available xenon UV flash lamp which, pursuant to the instant invention, is programmed to emit 30-150 joules of energy per pulse at a frequency of 20-50 Hz, with a further preferred pulse rate of 25-35 Hz. At a pulse rate above 25-30 Hz, the visible flicker of the emitted visible light is almost un-noticeable, appearing as a quasi-continuous light with no annoying pulsing-flash effect. Also, such UV pulse rates above 25-30 Hz, combined with the relatively low 30-150 joules of power per pulse, as employed in the present invention, produce a much softer, gentle humming sound during operation, avoiding the annoying loud popping/cracking sound commonly generated by prior art pulsed UV systems operating at lower pulsing rates and higher levels of power per pulse, such as, the prior art systems referenced above, which operate below 2 Hz and above 500 joules of power per pulse. The much softer sound generated by the operation of the present invention greatly reduces the discomfort and disturbance caused to people, often hospital patients, located in the vicinity of the room being disinfected.

Another aspect of the present invention is a software system, which may combine, among other functions, a control function (local and remote), a billing/record keeping function, a safety function, a scan the area to be treated function and a lamp life/output monitoring function. Using various sensors and hardware control units, the software system can, for example, track exactly the number and the energy of all UV pulses delivered during the life of a particular unit or lamp or during any particular cleaning step, thus enabling a bill by the number of UV pulses invoicing framework for the operation of the machine.

The wireless communication router or hub 56, using any suitable wireless protocol, is included as part of the hardware and software of this invention, allowing bi-directional communication with a wide range of remote accessories, sensors and controls.

In conjunction with optional remote or wired sensors, such as, door cards, motion 25s, occupancy sensors, temperature sensors, smoke sensors, ozone sensors, etc., the software can also implement an operational safety regime for the entire system, whereby the unit shuts down automatically if any dangerous conditions are encountered or detected by the remote sensors, e.g. motion/vibration detected at a door of the room being disinfected, signifying that a person is about to enter the room while the unit is operating, etc.

The software system may consist of different modules, e.g., the control system (central control unit 60, the motor control card 62 and the control cards box 54, located on the chassis hardware), other modules which may be located on a remote web server, and some of which are installed on a tablet, or other smart handheld device. An operator will preferentially use the tablet as the main remote user interface. The tablet positioned outside the room being disinfected communicates wirelessly, via any suitable wireless protocol such as WiFi, Bluetooth, RF, etc., with the communication hub 56 and the control system. The same tablet may also communicate, via a cellular data connection, e.g., GSM, 3G, LTE, etc., with a remote web server where some of the software functionality of this invention may be implemented, such as, tracking, billing, auditing, performance monitoring, record keeping, etc.

An optional GPS module on the tablet can relay to the remote webserver the precise location where each UV disinfection unit is deployed, enabling the remote webserver to offer centralized background processing and database services for a large number of UV disinfection units field-deployed anywhere in the world.

Typical Mode and Method of Operation for a Preferred Embodiment

In an exemplary mode and method of operation, an embodiment of this invention is used to disinfect the high touch surfaces in a hospital room, a typical source of germs which cause hospital acquired infections. The functional strength of this invention is for targeted surface disinfection of relatively smaller areas, as opposed to the whole room disinfection at once approach of the prior art systems. Indeed, objects such as equipment and furniture in a room being disinfected make one shot whole room disinfection almost impossible.

Typically, the targeted surface disinfection system unit is wheeled into a room which contains the target area to be disinfected by UV light. After orienting the unit toward the general target area and plugging in the unit's power cord into a wall AC power outlet, the operator leaves the room, places a motion sensing tag, e.g., door card, at the entrance door, and remotely initiates a disinfection cycle from the tablet.

Figure 2:
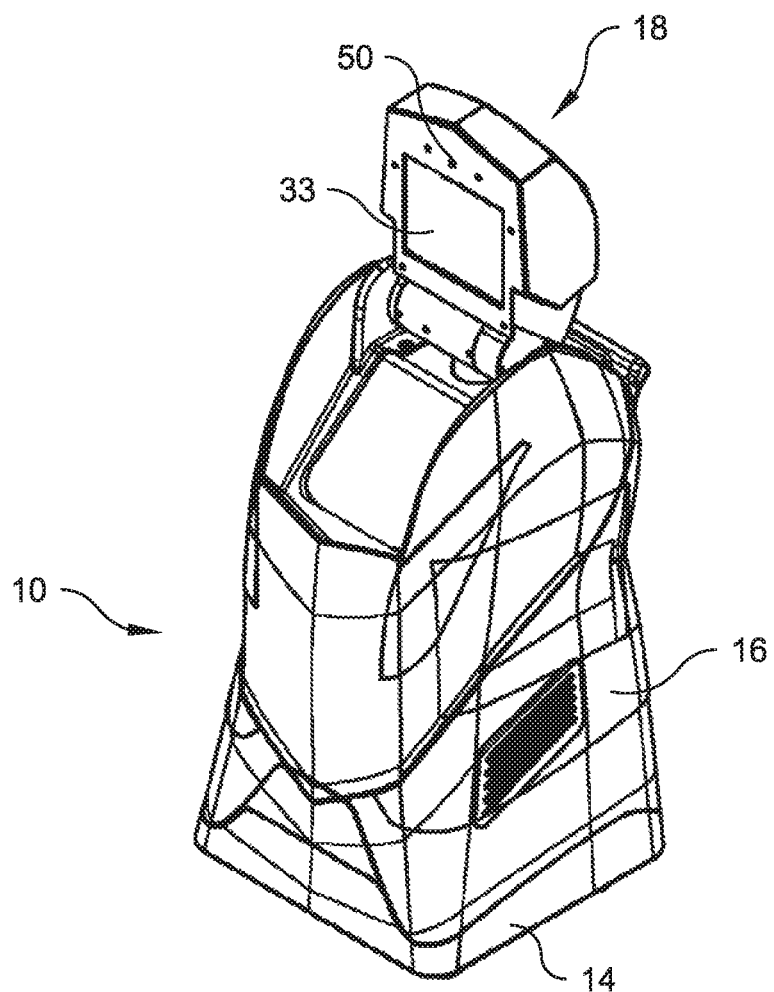
FIG. 2 is an isometric view of the surface disinfection system, similar to FIG. 1, but showing the head assembly in an operative position.

At the beginning of a UV disinfection cycle, the unit's head assembly 18 moves into its normal upright operating position, illustrated in FIGS. 2-3 by tilting up from of its stored folded down position, illustrated in FIG. 1. A pre-programmed number of UV flashes of a programmed intensity and pulse frequency are then delivered by the xenon lamp 30 to the target surface. Once the UV disinfection cycle has been completed, the motorized tilt mechanism 38 is actuated to tilt the head assembly 18 into its stored position.

During the UV disinfection process, the door card placed on the access door to the room continuously monitors for the detection of any movement at or around the door. Detection of movement or vibration around the door of the room being treated will result in an immediate emergency shut off of the system.

By using a tablet or a handheld smart device on which the control software is installed, the operator can remotely interact with the control system within the chassis 12, can select operational parameters, can initiate or stop all steps involved in the process, and can as well see inside the room by accessing the video camera 50.

An optional first step could consist of an automated scanning of the general target area by the control unit, or the operator can select a manual or preprogrammed xenon lamp flashing routine. The xenon lamp 30 is initially positioned perpendicular to the vertical axis and parallel to floor, but the operator can remotely pan, swivel and tilt the head assembly 18, in order to precisely direct the beam of UV light to the targeted surface to be disinfected.

The tablet may be programmed with a virtual joystick to enable the operator to remotely drive, direct and navigate the unit within the room by controlling the motors of the platform 14 so that multiple target surfaces may be disinfected without the need to re-enter the room to reposition the unit after each target surface has been disinfected.

Alternatively, the targeted surface disinfection system may be provided without remote controlled or autonomous robotic navigational capabilities. The principle of operation would be similar, however. After completing the disinfection of one target surface, the operator would reenter the room and manually reposition the unit in front of the next disinfection target surface, exit the room and remotely start the next disinfection cycle.

Various embodiments of this invention, with or without remote controlled or autonomous robotic navigational capabilities can be built with a common chassis and head assembly, which could then be fitted either on a non-motorized wheeled platform, or on the motorized robotic the wheeled platform 14. Each platform will have the same component dimensions to accommodate the chassis and head assembly. This modular construction offers flexibility and ensures that no major changes will be needed for the manufacturing either version of the unit.

Preferred Parameters of UV Irradiation

The xenon lamp 30 comprises an electrical U-shaped xenon UV discharge lamp placed behind the clear fused quartz window 33. No region of the emitted radiation is filtered in a preferred embodiment, due to the experimental observation that all regions of emitted radiation, i.e. UV-A, UV-B, UV-C and even the visible region, contribute positively to the disinfection process.

In contrast with the prior art trend of using high powered lamps (with emitted energies above 500 joules per pulse), the inventors herein made the surprising observation that better disinfection results (requiring less UV exposure time for germ inactivation) are achieved with a lower-power xenon UV discharge lamp of a typical emitted energy of 30-150 joules per pulse, by operating at a higher frequency of 20-50 Hz, compared to a frequency of less than 2 Hz used in the prior art. Additionally, in the prior art, energy per pulse varied as a function of frequency. If the frequency was decreased, the energy per pulse increased, while if the frequency was increased, the energy per pulse decreased, whereas pursuant to the invention, for a certain set of conditions the energy per pulse remains constant regardless of pulse frequency variations.

A preferred sub-range of pulse rate for the present invention is 25-35 Hz, with higher rates resulting in increased amperage draw. If the unit is to use regular AC wall outlets of the kind normally present in a typical hospital room (120 VAC and 15 A in N. America), the 15 A maximum current draw may become a limit that prevents pulse rates higher than 35-50 Hz from being achievable.

For targeted short-duration disinfection treatments, an alternative embodiment of the present invention may be powered entirely by on-board batteries or other type of rechargeable energy storage devices, without the need to be plugged in to an AC wall-outlet.

As shown in the experimental test values graphed in the FIG. 9, the xenon UV discharge lamp can maintain its energy output in the UV region at a reasonably high level, even with a 50 Hz pulse rate.

Figure 10:
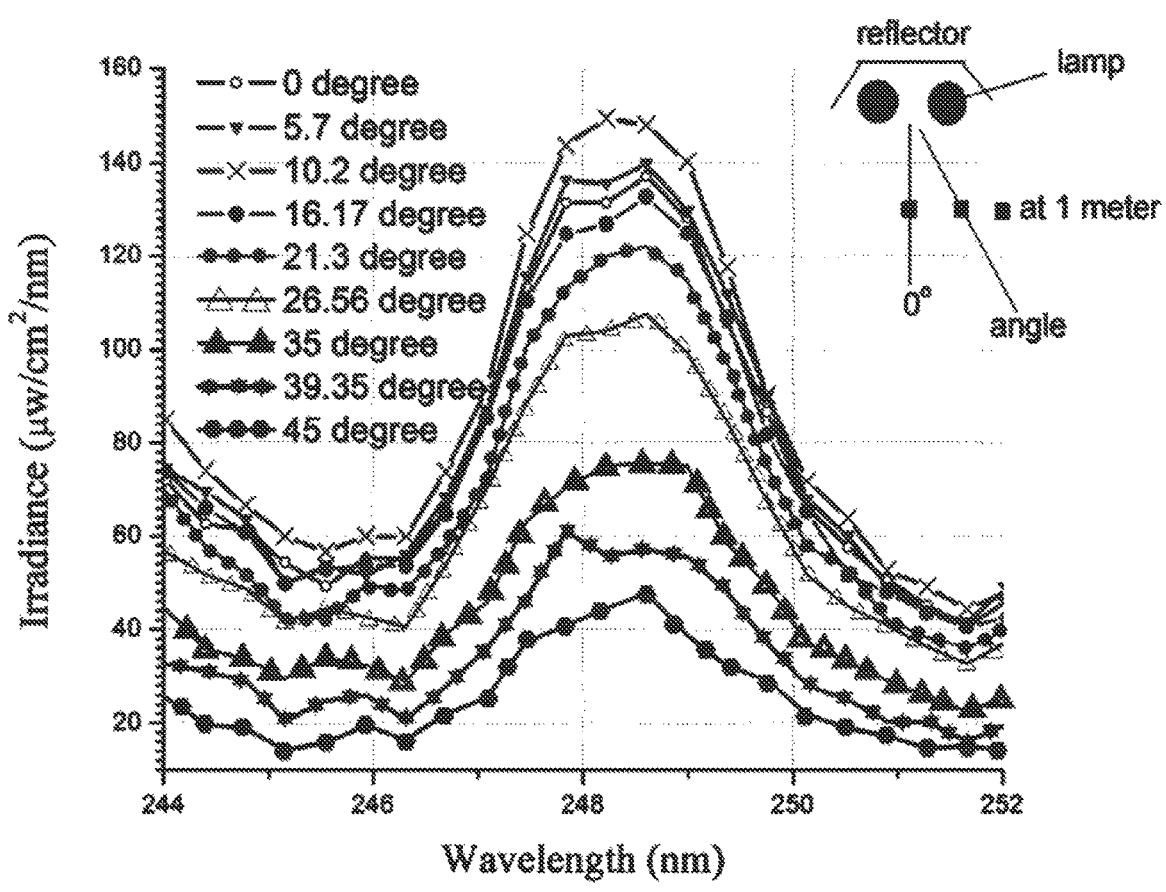
FIG. 10 is a graph of test results indicating xenon lamp energy output variance as a function of incident angles.

Further experimental tests performed by the inventors herein show that the presence of the reflector 40 is beneficial for focusing and guiding the bulk of the UV energy output towards the frontal direction of the beam (directly perpendicular to reflector). Experimental data graphed in the FIG. 10 shows how irradiance changes with the angle of the beam, proving that the energy output is much lower at various side angles compared to full frontal direction.

Figure 11:
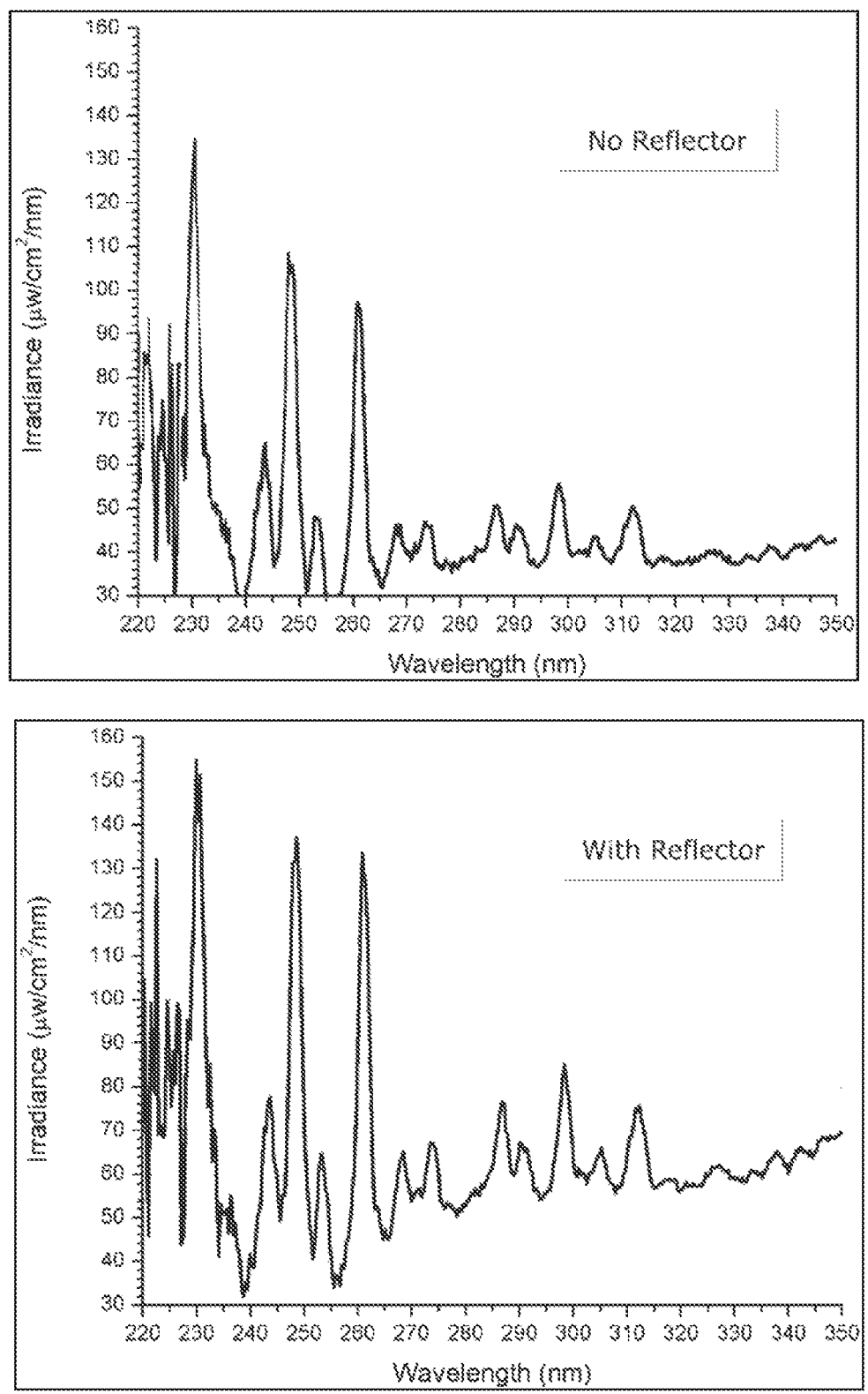
FIG. 11 a graph of test results indicating xenon lamp energy output with and without a reflector.

Further experimental data graphed in FIG. 11 shows how irradiance towards the target area directly in front of the UV emitter is much greater in the presence of a reflector, proving that the use of a reflector could directly lead to higher energy exposure and shorter exposure times for the same lamp nominal output.

For large rooms and general disinfection, a typical embodiment of the present invention is preferably positioned with the UV emitter at a distance of 10 feet from the target area, which could be covered by the UV beam up to a height of 10 feet in these circumstances; shorter distances are more effective, requiring a lower irradiation time for smaller target areas.

The table below displays experimental results that show a marked decrease of the required disinfection time with an increase of the pulsing frequency for the xenon UV discharge lamp of the present invention. Higher frequency significantly reduces the disinfection time; at 50 Hz (not shown in the table), the disinfection time is in the range of tens of seconds, rather than minutes.

| Frequency | Disinfection time (min) | Disinfection Efficiency |
|---|---|---|
| 5 Hz | 10 | 99.99% |
| 10 Hz | 5 | 99.98% |
| 20 Hz | 3 | 99.99% |
| 30 Hz | 2 | 99.99% |

The table below displays further experimental results showing disinfection efficiency, for UV treatment of MRSA and *B. Subtilis* with the present invention, to remain higher than 99%, even with reduced exposure times.

| Time (in seconds) | MRSA Efficiency | *B. Subtilis* Efficiency |
|---|---|---|
| 70 | 99.95% | 97.83% |
| 80 | 99.98% | 99.92% |
| 90 | 99.99% | 99.99% |

Especially when combined with a reduction in the distance between the UV emitter and the target area, the disinfection times can be reduced tremendously and still achieve satisfactory disinfection efficiency, a situation which is uniquely suited for the disinfection of high-touch surfaces in hospital rooms. When placed at a distance of 1 meter from the target area, the present invention achieved a disinfection efficiency of over 99% with very short exposure times, i.e., as little as 10 seconds. This very short disinfection cycle time is unparalleled in the prior art, and allows faster and more efficient disinfection of entire hospital rooms by disinfection of multiple small high-touch surfaces in a rapid succession of cycles using focused UV beams, rather than one very long cycle of disinfecting the entire room with a 360 degree UV beam.

Experimental results reported in the table below indicate the disinfection efficacy of the present invention on various pathogens and the dramatic reduction in disinfection time when the distance between the unit and the target surface is reduced from 10 feet to 5 feet. Indeed with respect to all species tested, the time required for 100% efficiency was reduced by at least one half.

| Species | Time (s) | Distance (ft) | Efficiency | Frequency (Hz) | Power (J) |
|---|---|---|---|---|---|
| *B. Subtilis* (1) | 60 | 10 | 85.10% | 25-35 | 30-150 |
| *B. Subtilis* | 120 | 10 | 99.01% | 25-35 | 30-150 |
| *B. Subtilis* | 180 | 10 | 100.00% | 25-35 | 30-150 |
| *B. Subtilis* | 30 | 5 | 100.00% | 25-35 | 30-150 |
| *B. Subtilis* | 60 | 5 | 100.00% | 25-35 | 30-150 |
| *B. Subtilis* | 120 | 5 | 100.00% | 25-35 | 30-150 |
| MRSA (2) | 60 | 10 | 99.88% | 25-35 | 30-150 |

-continued

| Species | Time (s) | Distance (ft) | Efficiency | Frequency (Hz) | Power (J) |
|---|---|---|---|---|---|
| MRSA | 120 | 10 | 100.00% | 25-35 | 30-150 |
| MRSA | 180 | 10 | 100.00% | 25-35 | 30-150 |
| MRSA | 30 | 5 | 100.00% | 25-35 | 30-150 |
| MRSA | 60 | 5 | 100.00% | 25-35 | 30-150 |
| MRSA | 120 | 5 | 100.00% | 25-35 | 30-150 |
| VRE (3) | 60 | 10 | 74.94% | 25-35 | 30-150 |
| VRE | 120 | 10 | 95.77% | 25-35 | 30-150 |
| VRE | 180 | 10 | 100.00% | 25-35 | 30-150 |
| VRE | 30 | 5 | 100.00% | 25-35 | 30-150 |
| VRE | 60 | 5 | 100.00% | 25-35 | 30-150 |
| VRE | 120 | 5 | 100.00% | 25-35 | 30-150 |
| c. Diff (4) | 60 | 10 | 98.50% | 25-35 | 30-150 |
| c. Diff | 120 | 10 | 100.00% | 25-35 | 30-150 |
| c. Diff | 180 | 10 | 100.00% | 25-35 | 30-150 |
| c. Diff | 30 | 5 | 98.50% | 25-35 | 30-150 |
| c. Diff | 45 | 5 | 100.00% | 25-35 | 30-150 |
| c. Diff | 50 | 5 | 100.00% | 25-35 | 30-150 |

Species Referens:
(1) *B. Subtilis* = *Bacillus subtilis*
(2) MRSA = Methicillin-resistant *Staphylococcus aureus*
(3) VRE = Vancomycin-resistant Enterococci
(4) *c. Diff* = *Clostridium difficile*

Door Card Safety Device

Also part of invention described herein, is a device and system for ensuring safe operation of the UV disinfection unit, by preventing humans from being exposed to UV radiation. A door card 80 is a battery powered small safety device, meant to be attached to the door of the room being disinfected, by hanging on the doorknob or by any other means, e.g., placing, leaning, etc. Various sensors can be embedded within the door card, e.g., motion sensor, acceleration sensor, shock sensor, IR proximity sensor, photo sensor, etc., to sense or detect movement in the proximity of the door card.

When placed by the door of the room being disinfected, the door card 80 communicates wirelessly with the central control unit 60. During operation, the door card 80 continuously monitors its sensor or sensors for the detection of any movement of the door or proximate the door.

When the unit is operating inside a room, safety requirements mandate that no person could be in that room and the access door to that room must be closed securely. Any movement of an access door could potentially signify that a person is inadvertently attempting to enter the room when it is unsafe to do so; in such a situation, the xenon lamp must be turned off immediately.

When movement (or vibration, shock, etc.) is detected above a set threshold on or around a door, the door card transmits a wireless signal which causes the control unit to immediately shut off the xenon lamp. After such an emergency shutdown, the UV disinfection operation can only be restarted after the UV disinfection unit and the door card are reset by the operator, and only if the door motion detection state reverts back to normal (no door movement detected).

In a typical embodiment, the door card 80 is powered by rechargeable battery, has a physical ON/OFF button, is fitted with wireless RF communication, has a 6-axis gyro sensor, and is controlled by an embedded microcontroller chip.

A typical mode of operation for the door card 80 is as follows:
The operator presses the ON/OFF switch, which turns on the microcontroller and central control unit communication;
the microcontroller searches for a hub and establishes communication with the central control unit 60;
the microcontroller calibrates itself depending on the position and alignment it currently is (such calibration may take about 20 seconds);
a certain threshold value for the acceleration is programmed within the microcontroller (but it could be changed/reprogrammed with special software);
once calibrated, the microcontroller starts to calculate acceleration in X, Y, Z directions and averages them to establish an overall acceleration;
the microcontroller continuously compares this acceleration to a threshold value; as long as this calculated acceleration is below the threshold, the microcontroller sends signals to the central control unit 60 indicating normal status;
when the measured acceleration increases above the threshold value for the first time, the microcontroller starts to monitor further readings to rule out a false alarm;
if the readings are above threshold continuously for a set amount of time, the microcontroller categorizes them as movement and sends a "door movement" signal to the central control unit 60 (which triggers an instant shut down of the xenon lamp).
once conditions go return to normal (door not moving), the microcontroller sends "normal" signals to the central control unit 60.

Thus it will be seen that there is provided a targeted surface disinfection system with pulsed UV light which achieves the various aspects, features and considerations of the present invention and which is well suited to meet the conditions of practical usage.

In the Figures of this application, in some instances, a plurality of elements may be shown as illustrative of a particular element, and a single element may be shown as illustrative of a plurality of a particular elements. Showing a plurality of a particular element is not intended to imply that a system or method implemented in accordance with the invention must comprise more than one of that element or step, nor is it intended by illustrating a single element that the invention is limited to embodiments having only a single one of that respective element. Those skilled in the art will recognize that the numbers of a particular element shown in a drawing can, in at least some instances, be selected to accommodate the particular user needs.

The particular combinations of elements and features in the above-detailed embodiment are exemplary only the interchanging and substitution of these teachings with other teachings in this and the incorporated-by-reference patents and applications are also expressly contemplated. As those skilled in the art will recognize, variations, modifications, and other implementations of what is described herein can occur to those of ordinary skill in the art without departing from the spirit and the scope of the invention as claimed.

Further, in describing the invention and in illustrating embodiments of the invention in the figures, specific terminology, numbers, dimensions, materials, etc., are used for the sake of clarity. However the invention is not limited to the specific terms, numbers, dimensions, materials, etc. so selected, and each specific term, number, dimension, material, etc., at least includes all technical and functional equivalents that operate in a similar manner to accomplish a similar purpose. Use of a given word, phrase, number, dimension, material, language terminology, product brand, etc. is intended to include all grammatical, literal, scientific, technical, and functional equivalents. The terminology used herein is for the purpose of description and not limitation.

All publications and references cited herein are expressly incorporated herein by reference in their entirety.

Having described the preferred embodiment of the invention, it will now become apparent to one of ordinary skill in the art that other embodiments incorporating their concepts may be used. Moreover, those of ordinary skill in the art will appreciate that the embodiment of the invention described herein can be modified, to accommodate and/or comply with changes and improvements in the applicable technology and standards referred to herein. For example, the technology can be implemented in many other, different, forms, and in many different environments, and the technology disclosed herein can be used in combination with other technologies. Variations, modifications, and other implementations of what is described herein can occur to those of ordinary skill in the art without departing from the spirit and the scope of the invention as claimed. It is felt therefore that the embodiment should not be limited to disclosed embodiment but rather should be limited only by the spirit and scope of the appended claims.

The particular combinations of elements and features in the above-detailed embodiment are exemplary only the interchanging and substitution of these teachings with other teachings in this and the referenced patents/applications are also expressly contemplated. As those skilled in the art will recognize, variations, modifications, and other implementations of what is described herein can occur to those of ordinary skill in the art without departing from the spirit and the scope of the invention as claimed. Accordingly, the foregoing description is by way of example only and is not intended as limiting. The invention's scope is defined in the following claims and the equivalents thereto.

Having thus described the invention, there is claimed as new and desired to be secured by Letters Patent:

1. A targeted surface disinfection system comprising a xenon UV lamp, a high voltage power supply for driving the xenon UV lamp and a pulse configuration control unit for configuring the output of the high voltage power supply, the xenon UV lamp, the high voltage power supply and the pulse configuration control unit being positioned on a mobile carriage, the pulse configuration control unit being programmed for driving the xenon UV lamp to emit UV radiant energy upon a target surface requiring disinfection, the targeted surface disinfection system further comprising an articulated head assembly and a chassis, the xenon UV lamp being mounted within the articulated head assembly, the chassis carrying the high voltage power supply and the pulse configuration control unit, the targeted surface disinfection system further including a vacuum pump carried by the chassis, a suction hose connected to the vacuum pump, the suction hose extending to the articulated head assembly for dissipating heat generated by the xenon UV lamp.

2. The targeted surface disinfection system in accordance with claim 1 wherein the articulated head assembly includes a heat sink for dissipating heat generated by the xenon UV lamp.

3. A method of disinfecting a target surface requiring disinfection with the targeted surface disinfection system of claim 1, the method comprising the steps of:
   a) moving the mobile carriage to within ten feet of the target surface,
   b) orienting the articulated head assembly such that the xenon UV lamp faces the target surface,
   c) emitting UV radiant energy upon the target surface, and
   d) terminating step c) after a duration sufficient for effective disinfection of the target surface.

4. The method of disinfecting a target surface requiring disinfection in accordance with claim 3 wherein the target surface requiring disinfection is contaminated with a pathogen selected from the group consisting of *Bacillus Subtilis*, Vancomycin Resistant Enterococci, MRSA or *Clostridium Difficile*.

5. A targeted surface disinfection system comprising a xenon UV lamp, a high voltage power supply for driving the xenon UV lamp and a pulse configuration control unit for configuring the output of the high voltage power supply, the xenon UV lamp, the high voltage power supply and the pulse configuration control unit being positioned on a mobile carriage, the pulse configuration control unit being programmed for driving the xenon UV lamp to emit between 30 and 150 joules of UV radiant energy upon a target surface requiring disinfection, the targeted surface disinfection system further comprising an articulated head assembly and a chassis, the xenon UV lamp and a reflector configured to reflect UV radiant energy emitted from the xenon UV lamp being mounted within the articulated head assembly, the articulated head assembly including a heat sink for dissipating heat generated by the xenon UV lamp and a fused quartz window, the xenon UV lamp being positioned behind the fused quartz window, the targeted surface disinfection system further including a vacuum pump carried by the chassis, a suction hose connected to the vacuum pump, the suction hose extending to the articulated head assembly for dissipating heat generated by the xenon UV lamp, UV radiant energy emitted from the xenon UV lamp and reflected from the reflector being transmitted through the fused quartz window and upon the target surface, the chassis carrying the high voltage power supply and the pulse configuration control unit.

6. A method of disinfecting a target surface requiring disinfection with the targeted surface disinfection system of claim 1, the method comprising the steps of:
   a) moving the mobile carriage to within ten feet of the target surface,
   b) orienting the articulated head assembly such that the xenon UV lamp faces the target surface,
   c) emitting UV radiant energy upon the target surface, and
   d) terminating step c) after a duration sufficient for effective disinfection of the target surface.

7. The method of disinfecting a target surface requiring disinfection in accordance with claim 6 wherein the target surface requiring disinfection is contaminated with a pathogen comprising *Bacillus Subtilis*, step a) includes placing the xenon UV lamp within five feet of the target surface and the duration of step d) comprises thirty seconds.

8. The method of disinfecting a target surface requiring disinfection in accordance with claim 6 wherein the target surface requiring disinfection is contaminated with a pathogen comprising MRSA, step a) includes placing the xenon UV lamp within five feet of the target surface and the duration of step d) comprises thirty seconds.

9. The method of disinfecting a target surface requiring disinfection in accordance with claim 6 wherein the target surface requiring disinfection is contaminated with a pathogen comprising Vancomycin Resistant Enterococci, step a) includes placing the xenon UV lamp within five feet of the target surface and the duration of step d) comprises thirty seconds.

10. The method of disinfecting a target surface requiring disinfection in accordance with claim 6 wherein the target surface requiring disinfection is contaminated with a pathogen comprising *Clostridium Difficile*, step a) includes placing the xenon UV lamp within five feet of the target surface and the duration of step d) comprises forty five seconds.

11. The method of disinfecting a target surface requiring disinfection in accordance with claim 6 wherein the target surface requiring disinfection is contaminated with a pathogen comprising *Bacillus Subtilis* or Vancomycin Resistant Enterococci, step a) includes placing the xenon UV lamp within ten feet of the target surface and the duration of step d) comprises one hundred eighty seconds.

12. The method of disinfecting a target surface requiring disinfection in accordance with claim 6 wherein the target surface requiring disinfection is contaminated with a pathogen comprising MRSA or *Clostridium Difficile*, step a) includes placing the xenon UV lamp within ten feet of the target surface and the duration of step d) comprises one hundred twenty seconds.

13. A targeted surface disinfection system comprising a xenon UV lamp, a high voltage power supply for driving the xenon UV lamp and a pulse configuration control unit for configuring the output of the high voltage power supply, the xenon UV lamp, the high voltage power supply and the pulse configuration control unit being positioned on a motorized mobile carriage, the pulse configuration control unit being programmed for driving the xenon UV lamp to emit between 30 and 150 joules of UV radiant energy upon a target surface requiring disinfection, the targeted surface disinfection system further comprising an articulated head assembly and a chassis, the xenon UV lamp and a reflector configured to reflect UV radiant energy emitted from the xenon UV lamp being mounted within the articulated head assembly, the articulated head assembly including a fused quartz window, the xenon UV lamp being positioned behind the fused quartz window, UV radiant energy emitted from the xenon UV lamp and reflected from the reflector being transmitted through the fused quartz window and upon the target surface, the chassis carrying the high voltage power supply and the pulse configuration control unit, the articulated head assembly including a video camera and the chassis including a hub and a central control unit programmed for remote control of the operation of the targeted surface disinfection system after placement within a room having one or more target surfaces requiring disinfection.

14. The targeted surface disinfection system in accordance with claim 13 wherein the articulated head assembly includes a heat sink for dissipating heat generated by the xenon UV lamp.

15. The targeted surface disinfection system in accordance with claim 13, the chassis including a journal mounted for rotation about a vertical axis relative to the chassis and a motor operatively connected to the journal for rotating the journal, the articulated head assembly being connected to the journal, whereby the articulated head assembly is rotatable about the vertical axis relative to the chassis, the articulated head assembly further including a motorized tilt mechanism for rotating the articulated head assembly about a horizontal axis relative to the chassis, the motorized tilt mechanism interconnecting the articulated head assembly to the journal, whereby the articulated head assembly is rotatable about the vertical axis relative to the chassis and about the horizontal axis relative to the chassis to an operative position, wherein the xenon UV lamp faces the target surface.

16. The targeted surface disinfection system in accordance with claim 15 wherein the chassis is enclosed within a cabinet, the cabinet including a recess, the articulated head assembly being rotatable about the vertical axis and about the horizontal axis relative to the chassis to a retracted storage position, wherein the articulated head assembly is received within the cabinet recess.

17. The targeted surface disinfection system in accordance with claim 13 further including a door card, the door card including at least one sensor for detecting attempted opening of a door to a room wherein the targeted surface disinfection system is in operation, the door card further comprising a microcontroller in monitoring communication with the at least one sensor for determining attempted entry to the room and in wireless communication with the central control unit, the microcontroller transmitting a wireless shut down signal to the central control unit when a determination is made that entry to the room is about to be attempted.

18. The targeted surface disinfection system in accordance with claim 13 further including a vacuum pump carried by the chassis, a suction hose connected to the vacuum pump, the suction hose extending to the articulated head assembly for dissipating heat generated by the xenon UV lamp.

19. A method of disinfecting a target surface requiring disinfection with the targeted surface disinfection system of claim 13, the method comprising the steps of:
   a) moving the motorized mobile carriage to within ten feet of the target surface,
   b) orienting the articulated head assembly such that the xenon UV lamp faces the target surface,
   c) emitting UV radiant energy upon the target surface, and
   d) terminating step c) after a duration sufficient for effective disinfection of the target surface.

20. A method of disinfecting a target surface requiring disinfection with the targeted surface disinfection system of claim 15, the method comprising the steps of:
   a) employing the video camera and the central control unit to move the motorized mobile carriage to within ten feet of the target surface,
   b) employing the motor operatively connected to the journal and the motorized tilt mechanism to orient the articulated head assembly such that the xenon UV lamp faces the target surface,
   c) emitting UV radiant energy upon the target surface, and
   d) terminating step c) after a duration sufficient for effective disinfection of the target surface.

* * * * *